(12) United States Patent
Kröpke et al.

(10) Patent No.: US 7,906,151 B2
(45) Date of Patent: Mar. 15, 2011

(54) COSMETIC PREPARATION CONTAINING A STABILIZED PRESERVATIVE

(75) Inventors: Rainer Kröpke, Schenefeld (DE); Astrid Heptner, Hamburg (DE); Stephanie Von Der Fecht, Schenefeld (DE); Jens Nielsen, Henstedt-Ulzburg (DE); Celina Storbeck, Bönningstedt (DE)

(73) Assignee: Beiersdorf AG, Hamburg (DE)

( * ) Notice: Subject to any disclaimer, the term of this patent is extended or adjusted under 35 U.S.C. 154(b) by 1357 days.

(21) Appl. No.: 10/864,480

(22) Filed: Jun. 10, 2004

(65) Prior Publication Data

US 2005/0048019 A1  Mar. 3, 2005

(30) Foreign Application Priority Data

Jun. 14, 2003 (DE) .................. 103 26 899

(51) Int. Cl.
*A61K 33/00* (2006.01)
*A61K 8/00* (2006.01)
*A61K 8/18* (2006.01)

(52) U.S. Cl. ........... 424/600; 424/488; 424/401; 514/57; 514/772

(58) Field of Classification Search .................. None
See application file for complete search history.

(56) References Cited

U.S. PATENT DOCUMENTS

| | | | |
|---|---|---|---|
| 3,649,302 A * | 3/1972 | Daggy et al. .................. 426/271 |
| 3,758,686 A | 9/1973 | Sieger et al. |
| 4,024,290 A * | 5/1977 | Layton .......................... 426/548 |
| 4,146,652 A | 3/1979 | Kahn et al. |
| 4,154,863 A | 5/1979 | Kahn et al. |
| 4,158,055 A | 6/1979 | Shultz et al. |
| 4,199,604 A | 4/1980 | Kahn et al. |
| 4,199,605 A | 4/1980 | Kahn et al. |
| 4,216,242 A * | 8/1980 | Braverman .................. 426/573 |
| 4,234,611 A | 11/1980 | Kahn et al. |
| 4,237,146 A | 12/1980 | Kahn et al. |
| 4,244,976 A | 1/1981 | Kahn et al. |
| 4,244,977 A | 1/1981 | Kahn et al. |
| 4,308,287 A | 12/1981 | Kahn et al. |
| 4,350,711 A | 9/1982 | Kahn et al. |
| 4,390,550 A | 6/1983 | Kahn et al. |
| 4,425,329 A * | 1/1984 | Tsutsumi et al. .............. 514/772 |
| 4,756,919 A * | 7/1988 | Cirigiano et al. ............. 426/330 |
| 4,940,588 A | 7/1990 | Sparks et al. |
| 4,952,402 A | 8/1990 | Sparks et al. |
| 4,963,385 A * | 10/1990 | Antrim et al. ................ 426/602 |
| 5,075,113 A * | 12/1991 | DuBois ........................ 424/450 |
| 5,104,674 A * | 4/1992 | Chen et al. ................... 426/573 |
| 5,132,128 A * | 7/1992 | Rockland ..................... 426/658 |
| 5,260,083 A * | 11/1993 | Brain et al. .................. 426/573 |
| 5,338,562 A * | 8/1994 | Humphreys .................. 426/603 |
| 5,965,179 A | 10/1999 | Ducret et al. |
| 5,997,887 A * | 12/1999 | Ha et al. ........................ 424/401 |
| 6,022,896 A | 2/2000 | Weinkauf et al. |
| 6,042,841 A | 3/2000 | Alaluf et al. |
| 6,120,758 A * | 9/2000 | Siddiqui et al. ............ 424/78.02 |
| 6,316,010 B2 * | 11/2001 | Deckner et al. .............. 424/401 |
| 6,365,175 B1 | 4/2002 | Alaluf et al. |
| 6,495,718 B1 | 12/2002 | Schmidt |
| 6,541,606 B2 * | 4/2003 | Margolin et al. ............. 530/350 |
| 6,790,451 B2 * | 9/2004 | Nakanishi ..................... 424/401 |
| 6,805,874 B1 * | 10/2004 | Lutz et al. .................... 424/401 |
| 6,844,303 B2 * | 1/2005 | Lange .......................... 510/130 |
| 6,849,251 B2 * | 2/2005 | Banowski et al. .............. 424/65 |

FOREIGN PATENT DOCUMENTS

| | | |
|---|---|---|
| DE | 2858023 | 8/1978 |
| DE | 3538429 | 4/1986 |
| DE | 68902863 | 4/1993 |
| DE | 9922538 | 11/2000 |
| DE | 9928495 | 12/2000 |
| DE | 69614088 | 11/2001 |
| EP | 0749749 | 12/1996 |
| EP | 1013178 | 6/2000 |
| JP | 55-162710 | 12/1980 |

OTHER PUBLICATIONS

English Language Abstract of JP 55-162710.
Bährle-Rapp, M.: Springer-Lexikon, Kosmetik und Körperpflege, 2001, p. 400, ISBN: 3-540-67888-3.
Raab, Wolfgang: Pflegekosmetik, 2. Aufl., 1997, p. 131, ISBN: 3-7741-0641-X GOVI.
English Language Abstract of DE 19922538.
English Language Abstract of EP 0749749.

* cited by examiner

*Primary Examiner* — Robert A Wax
*Assistant Examiner* — Melissa S Mercier
(74) *Attorney, Agent, or Firm* — Greenblum & Bernstein, P.L.C.

(57) ABSTRACT

Cosmetic or dermatological composition comprising potassium sorbate and at least one stabilizing agent selected from microcrystalline cellulose, talc and a lipid having an interfacial tension of at least about 10 mN/m.

44 Claims, No Drawings

COSMETIC PREPARATION CONTAINING A STABILIZED PRESERVATIVE

CROSS-REFERENCE TO RELATED APPLICATIONS

The present application claims priority under 35 U.S.C. §119 of German Patent Application No. 103 26 899.5, filed on Jun. 14, 2003, the disclosure of which is expressly incorporated by reference herein in its entirety.

BACKGROUND OF THE INVENTION

1. Field of the Invention

The invention relates to cosmetic or dermatological preparations comprising potassium sorbate as preservative and microcrystalline cellulose and/or talc and/or, on the basis of W/O or W/S emulsions, non- or mid-polar lipids as stabilizing agents.

2. Discussion of Background Information

The antimicrobial effect of sorbic acid has been known since 1939. The derivatives of sorbic acid used are primarily the alkali metal salts as preservatives, especially in the food sector. The particular advantage of the alkali metal sorbates is their good solubility in water. Sorbic acid and their potassium and/or sodium salt are recommended as preservatives, mostly in amounts of 0.05-0.2% by weight, for pharmaceutical and cosmetic preparations (E. & P. Pelle, Gyogyszzereszet 15, 94 [1971] [hun]; C.A. 75, 52752 [1971]). As known from diverse investigations, in contrast to other preservatives, sorbic acid and the alkali metal sorbates behave extremely favorably with regard to the toxicological properties. Neither sorbic acid nor potassium sorbate are carcinogenic, mutagenic or teratogenic.

Since sorbic acid and the alkali metal sorbates are used as preservatives for cosmetics, their tolerability by the skin has also been studied and no negative properties at all have been found. The properties of sorbic acid and/or of potassium sorbate, which is preferably suitable for preserving cosmetic compositions which have been rendered acidic, can be found, for example, in E. Lück & K. Remmert, SÖFW 118, 699 [1992]. The World Health Organisation has documented the acceptability of sorbic acid and/or alkali metal sorbates by the fact that it has fixed for these substances the highest value of the acceptable daily dose for preservatives, i.e., 25 mg/kg of body weight.

Due to the physiological acceptability, sorbic acid and alkali metal sorbates are used in preserving articles which come into contact with human or animal skin during production, processing or use.

It is known that in cosmetics potassium sorbate degrades and leaves behind a very unpleasant odour which can be detected even in trace amounts. The oxidative degradation products can also lead to discoloration problems, meaning that potassium sorbate cannot be used in cosmetics on its own or with the customary preservatives. It is known to add stabilizers such as allantoin or BHT to the preparation to avoid these unacceptable aspects of cosmetics which contain potassium sorbate. BHT is a synthetically prepared antioxidant and preservative. BHT, being a toluene derivative, is not regarded as being completely uncritical in toxicological terms, and is used in cosmetics only in exceptional cases. In particular, BHT should not be used in cosmetics for people with allergies.

Allantoin is a skin-smoothing active ingredient with only a low stabilizing potential, rendering it unsuitable for use as a stabilizing agent for preservatives.

It would be desirable to have available a cosmetic or dermatological composition which comprises potassium sorbate as preservative and nevertheless does not have the disadvantages of the potassium sorbate containing preparations known from the prior art. In particular, it would be advantageous to have available a composition which comprises only small amounts of preservative and added stabilizers.

SUMMARY OF THE INVENTION

The present invention provides a cosmetic or dermatological composition which comprises potassium sorbate and a stabilizer therefor. The stabilizer comprises microcrystalline cellulose and/or talc and/or a lipid exhibiting an interfacial tension of at least about 10 mN/m.

In one aspect, the composition may comprise from about 0.001% to about 1% by weight of potassium sorbate, e.g., from about 0.01% to about 0.6%, or from about 0.05% to about 0.2% by weight of potassium sorbate. (Unless stated otherwise, the weight percentages given herein and in the appended claims are based on the total weight of the composition).

In another aspect, the composition may comprise at least one of microcrystalline cellulose and talc, preferably in a total amount of from about 0.01% to about 5% by weight, e.g., from about 0.1% to about 1% by weight. For example, the composition may comprise from about 0.1% to about 1% by weight of microcrystalline cellulose and/or the composition may comprise from about 0.1% to about 1% by weight of talc.

In yet another aspect, the composition may comprise microcrystalline cellulose having a molecular weight of from about 20,000 to about 80,000 g/mol, for example, microcrystalline cellulose having a molecular weight of from about 30,000 to about 50,000 g/mol.

In a still further aspect, the composition may comprise microcrystalline cellulose having a particle size of from about 1 μm to about 100 μm, e.g., a particle size of from about 10 μm to about 50 μm.

In another aspect, the composition may be based on a W/O emulsion or on a W/S emulsion and may comprise one or more lipids exhibiting an interfacial tension of at least about 10 mN/m.

In yet another aspect of the composition of the present invention, the composition may further comprise dehydracetic acid and/or a salt thereof, e.g., in an amount of from about 0.01% to about 2% by weight, preferably, in an amount of from about 0.05% to about 1% by weight. For example, the composition may comprise the sodium salt of dehydracetic acid.

In another aspect, the composition may further comprise benzyl alcohol, preferably in an amount of from about 0.1% to about 2.0% by weight.

In yet another aspect, the composition may further comprise a citrate buffer and/or a lactate buffer. For example, the citrate buffer may comprise citric acid:sodium citrate in a ratio of about 1:2 and/or the lactate buffer may comprise lactic acid:sodium lactate in a ratio of about 1:2.

In another aspect, the composition may further comprise one or more electrolytes, preferably in an amount of from about 0.1% to about 5.0% by weight. For example, the one or more electrolytes may comprise sodium chloride and/or magnesium sulfate.

In a still further aspect of the composition of the present invention, the composition may comprise from about 0.05% to about 1% by weight of potassium sorbate and (a) from about 0.1% to about 5% by weight of microcrystalline cellulose and/or (b) from about 0.1% to about 5% by weight of talc.

For example, the composition may comprise microcrystalline cellulose having a molecular weight of from about 30,000 to about 50,000 g/mol and/or a particle size of from about 10 μm to about 50 μm. Preferably, the composition may further comprise dehydracetic acid and/or a salt thereof and/or benzyl alcohol and/or a citrate buffer (e.g., a buffer comprising citric acid:sodium citrate in a ratio of about 1:2) and/or a lactate buffer (e.g., a buffer comprising lactic acid:sodium lactate in a ratio of about 1:2) and/or one or more electrolytes. For example, the composition may further comprise from about 0.05% to about 1% by weight of the sodium salt of dehydracetic acid and/or from about 0.1% to about 2.0% by weight of benzyl alcohol and/or from about 0.1% to about 5.0% by weight of sodium chloride and/or magnesium sulfate.

The present invention also comprises a cosmetic which comprises the composition of the present invention (including the various aspects thereof). By way of non-limiting example, the cosmetic may comprise a lotion, a cream, an impregnation solution, a spray or an aerosol.

The present invention also provides a method of stabilizing potassium sorbate in a cosmetic or dermatological composition. The method comprises incorporating into the composition microcrystalline cellulose and/or talc and/or a lipid having an interfacial tension of at least about 10 mN/m in an amount which is sufficient for stabilizing the potassium sorbate at least to a certain extent.

In one aspect of the method, the composition may comprise from about 0.001% to about 1% by weight of potassium sorbate, and microcrystalline cellulose and/or talc may be incorporated therein in an amount of from about 0.01% to about 5% by weight.

In another aspect, the composition may be based on a W/O emulsion or on a W/S emulsion and the method may comprise incorporating into the composition one or more lipids having an interfacial tension of at least about 10 mN/m in an amount which is sufficient for stabilizing the potassium sorbate at least to a certain extent. For example, this composition may comprise from about 0.001% to about 1% by weight of potassium sorbate and/or the one or more lipids may comprise at least one lipid having an interfacial tension of at least about 20 mN/m, preferably at least about 30 mN/m.

Surprisingly, it has been found that cosmetic or dermatological preparations comprising potassium sorbate and one or more stabilizing agents selected from microcrystalline cellulose, talc and, particularly if the preparation is based on a W/O or W/S emulsion, lipids with an interfacial tension greater than or equal to about 10 mN/m, have excellent preserving properties. In particular, the preparations according to the invention do not have the numerous disadvantages of the potassium sorbate containing preparations of the prior art. Substantially no odour or discoloration problems of any kind arise when the preparations according to the invention are used as cosmetics.

The combination of potassium sorbate as preservative with the above-mentioned stabilizers leads, moreover, to very skin-compatible preservative systems, meaning that skin-unfriendly systems, such as, for example, parabens, Germal II (formaldehyde donor), Kathon CG, may be dispensed with.

Potassium sorbate may be very readily stabilized by microcrystalline cellulose and/or talc in cosmetic preparations. In W/O or W/S preparations, which comprise exclusively non-polar to mid-polar lipid components, such as, for example, isoeicosane, C5-cyclomethicones, mineral oil, this stabilizing property has likewise been established. In such preparations, potassium sorbate develops a good microbicidal action and an oxidation to substances with unpleasant odours is suppressed and/or significantly delayed.

Microcrystalline cellulose has been known as a cosmetic-pharmaceutical adjuvant for a relatively long time. It is generally used as a filler and binder in tablets, and also as a suspending agent and/or thickener in cosmetic and/or pharmaceutical preparations (H. P. Fiedler; Lexikon der Hilfsstoffe für Pharmazie, Kosmetik und angrenzende Gebiete [Lexicon of auxiliaries for pharmacy, cosmetics and related fields], Editio Cantor Verlag, 5$^{th}$ Edition 2002). Thus, for example, JP 55162710 describes cosmetic emulsions comprising microcrystalline cellulose. However, the stabilizing advantages of potassium sorbate containing preparations is not disclosed in any of the documents.

The microcrystalline cellulose is preferably selected from cellulose types which have a molecular weight of from about 20,000 to about 80,000 g/mol, in particular a molecular weight of not less than about 30,000 and/or not higher than about 50,000 g/mol. Cellulose types which are particularly advantageous are characterized by particle sizes of from about 1 μm to about 100 μm, in particular not less than about 10 μm and/or not more than about 50 μm. Preferred microcrystalline celluloses as commercial products are available, for example, under the trade name Avicel®.

Talc is a widespread hydrated magnesium silicate of the composition $Mg_3[(OH)_2/Si_4O_{10}]$ or $3MgO.4SiO_2.H_2O$. The hydrophobic character and the good absorption capacity of talc is essential for many applications of talc, such as, for example, in cosmetics or for rubbing into the hands when doing gymnastics.

The stabilizers microcrystalline cellulose and/or talc are preferably used in amounts of from about 0.01% to about 5% by weight, e.g., of not less than about 0.1% and/or not more than about 1% by weight, based on the total weight of the preparation.

Even the addition of such small amounts of stabilizers permits effective stabilization of the potassium sorbate containing cosmetic preparations.

Potassium sorbate may advantageously be contained in amounts of from about 0.001% to about 1% by weight, preferably from about 0.01% to about 0.6% by weight, particularly preferably from about 0.05% to about 0.2% by weight, based on the total weight of the preparation. The amount of potassium sorbate added to cosmetics is also prescribed by law in some countries.

In addition to the stabilizers according to the invention, other stabilizers known to the person skilled in the art may further be contained in the composition of the present invention, as long as they do not significantly interfere with the advantages provided by the present invention.

The presence of salts, in particular the sodium salt of dehydracetic acid, and/or of benzyl alcohol has proven to be particularly advantageous.

The stabilization of the potassium sorbate with benzyl alcohol and/or (the sodium salt of) dehydracetic acid affords a synergistic effect.

Since dehydracetic acid (DHA, 3-acetyl-6-methyl-2[H]pyran-2,4[3H]-dione, 3[1-hydroxyethylidene]-6-methyl-2[H]-pyran-2,4[3H]-dione) of the structural formula

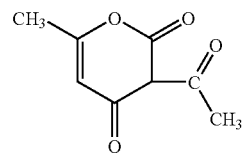

is relatively highly effective even at a relatively high pH, DHA and its salts are recommended for preserving pharmaceutical and cosmetic preparations, in particular in amounts of from about 0.05% to about 0.15% by weight. The sodium salt of dehydracetic acid is likewise preferably used as stabilizing additive for the cosmetic preparations according to the invention. Indications as to its suitability as stabilizing agent are given, for example, in C. A. Bennassi et al., Int. J. Cosmet. Sci. 10, 29 [1988]; C. A. 109, 155934 [1988].

The preferred concentrations of salts of dehydracetic acid, preferably the sodium salt, are from about 0.05% to about 1.0% by weight, and those of benzyl alcohol are from about 0.1% to about 2.0% by weight, based on the total weight of the preparation.

A pH buffer in the range 4-6 also has a very good synergistically stabilizing effect. For this purpose, a citrate buffer, advantageously comprising citric acid:sodium citrate in a ratio of about 1:2, and a lactate buffer, advantageously comprising lactic acid:sodium lactate in a ratio of about 1:2, haven proven particularly useful.

These buffer mixtures may be added to the preparations according to the invention and increase enormously the stabilizing effect of the stabilizers microcrystalline cellulose and/or talc. The effectiveness of the sorbates is significantly increased through the buffering by the buffer mixtures since the sorbates can penetrate the cell wall and can develop their effect inside the cell. These properties are made easier by an acidic medium.

In addition, it has proven particularly advantageous when the preparation additionally comprises electrolytes in an amount of from about 0.1% to about 5.0% by weight, based on the total weight of the preparation. In this case, the preparations according to the invention exhibit improved user-friendly properties and, in particular, the stabilization of the preservative is increased. Preferred electrolytes are sodium chloride and/or magnesium sulfate.

The preparations which are based on a W/O or W/S emulsion and which comprise lipids with an interfacial tension of greater than or equal to 10 mN/m besides potassium sorbate are also in accordance with the present invention. Surprisingly, these lipids also exhibit a stabilizing effect for potassium sorbate in cosmetics.

For the purposes of the present disclosure, the expression "lipids" is sometimes used as the generic term for fats, oils, waxes and the like, as known to the person skilled in the art. Also the terms "oil phase" and "lipid phase" are used synonymously herein.

Oils and fats differ from one another in their polarity, which is difficult to define. It has already been proposed to adopt interfacial tension towards water as a measure of the polarity index of an oil or of an oil phase. This means that the greater the polarity of the oil phase in question, the lower the interfacial tension between this oil phase and water. According to the invention, the interfacial tension is regarded as being a possible measure of the polarity of a given oil component.

The interfacial tension is the force which acts upon an imaginary line of one meter in length positioned in the interface between two phases. The physical unit for this interfacial tension is calculated classically according to the force/length relationship and is usually given in mN/m (millinewtons divided by meters). It has a positive sign when it strives to reduce the interfacial area. In the reverse case, it has a negative sign. For the purposes of the present invention, polar lipids are considered as being lipids whose interfacial tension towards water is less than about 10 mN/m, and nonpolar lipids are considered to be those whose interfacial tension towards water is more than about 30 mN/m. Lipids with an interfacial tension towards water between about 10 and about 30 mN/m are generally referred to as mid-polar.

It thus follows that lipids with an interfacial tension of >about 30 mN/m are referred to as nonpolar, those with a tension of from about 10 to about 30 mN/m as mid-polar and those with a tension of <about 10 mN/m as polar.

Polar oils are, for example, those from lecithins and of fatty acid triglycerides, namely the triglycerol esters of saturated and/or unsaturated, branched and/or unbranched alkanecarboxylic acids with a chain length of from about 8 to 24, in particular about 12 to 18 carbon atoms.

The oil phase of the present emulsion may therefore be selected from, for example, dialkyl ethers, saturated or unsaturated, branched or unbranched alcohols. It is particularly advantageous when the oil phase has a content of $C_{12-15}$-alkyl benzoate, or consists entirely thereof.

In addition, the oil phase can advantageously be selected from Guerbet alcohols. Guerbet alcohols are named after Marcel Guerbet, who described their preparation for the first time. They are formed in accordance with the reaction equation

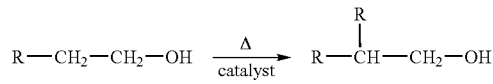

by oxidation of an alcohol to form an aldehyde, by aldol condensation of the aldehyde, elimination of water from the aldol and hydrogenation of the allyl aldehyde. Guerbet alcohols are themselves liquid at low temperatures and cause virtually no skin irritations. They can advantageously be used as fatting, superfatting and also refatting constituents in skin care and hair care compositions.

The use of Guerbet alcohols in cosmetics is known per se. Such species are mostly characterized by the structure

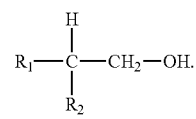

Here, $R_1$ and $R_2$ are generally unbranched alkyl radicals.

The Guerbet alcohol or the Guerbet alcohols are advantageously selected according to the invention from the group in which $R_1$=propyl, butyl, pentyl, hexyl, heptyl or octyl and $R_2$=hexyl, heptyl, octyl, nonyl, decyl, undecyl, dodecyl, tridecyl or tetradecyl.

Guerbet alcohols which are preferred according to the invention include 2-butyloctanol of the chemical structure

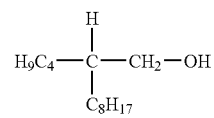

which is available, for example, under the trade name Isofol® 12 from Condea Chemie GmbH, and 2-hexyldecanol of the chemical structure

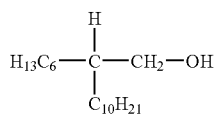

which is available, for example, under the trade name Isofol® 16 from Condea Chemie GmbH. Mixtures of Guerbet alcohols may also be used advantageously in accordance with the invention. Mixtures of 2-butyloctanol and 2-hexyldecanol are available, for example, under the trade name Isofol® 14.

The total amount of Guerbet alcohols in the finished cosmetic or dermatological preparations is advantageously up to about 25.0% by weight, preferably from about 0.5% to about 15.0% by weight, based on the total weight of the preparations.

Any mixtures of such oil and wax components may also be used advantageously for the purposes of the present invention. It may also in some cases be advantageous to use waxes, for example cetyl palmitate, as the sole lipid component of the oil phase.

Particularly advantageous mid-polar lipids for the purposes of the present invention include the substances listed below:

| Trade name | INCI name | Polarity [mN/m] |
|---|---|---|
| DUB VCI 10 | Isodecyl Neopentanoate | 29.9 |
| Dermol IHD | Isohexyl Decanoate | 29.7 |
| Dermol 108 | Isodecyl Octanoate | 29.6 |
| Dihexyl ether | Dihexyl Ether | 29.2 |
| Dermol 109 | Isodecyl 3,5,5 Trimethyl Hexanoate | 29.1 |
| Cetiol SN | Cetearyl Isononanoate | 28.6 |
| Isopropyl palmitate | Isopropyl Palmitate | 28.8 |
| DC Fluid 345 | Cyclomethicone | 28.5 |
| Dow Corning Fluid 244 | Cyclopolydimethylsiloxane | 28.5 |
| Jojoba oil gold | | 26.2 |
| Wacker AK 100 | Dimethicone | 26.9 |
| Dermol 98 | 3,5,5-Trimethyl 2-Ethylhexanoate | 26.2 |
| Dow Corning Fluid 246 | Open | 25.3 |
| Eutanol G | Octyldodecanol | 24.8 |
| Isofol 16 | Hexyl Decanol | 24.3 |
| Dermol 139 | Isotridecyl 3,5,5-Trimethylhexanonanoate | 24.5 |
| Cetiol PGL | Hexyldecanol (+) Hexyl Decyl Laurate | 24.3 |
| Cegesoft C24 | Octyl Palmitate | 23.1 |
| M.O.D. | Octyldodecyl Myristate | 22.1 |
| Macadamia Nut Oil | | 22.1 |
| Silicone oil VP 1120 | Phenyl Trimethicone | 22.7 |
| Isocarb 12 | Butyl Octanoic acid | 22.1 |
| Isopropyl stearate | Isopropyl Stearate | 21.9 |
| Finsolv TN | C12-15 Alkyl Benzoate | 21.8 |
| Dermofeel BGC | Butylene Glycol Caprylate/Caprate | 21.5 |
| Miglyol 812 | Caprylic/Capric Triglyceride | 21.3 |
| Trivent OCG | Tricaprylin | 20.2 |
| Dermol 866 | PEG Diethyl Hexanoate/ Diisononanoate/ Ethylhexyl Isononanoate | 20.1 |
| Isofol 14T | Butyl Decanol (+) Hexyl Octanol (+) Hexyl Decanol (+) Butyl Octanol | 19.8 |
| Lipovol MOS-130 | Tridecyl Stearate(+) Tridecyl Trimellitate (+) Dipentaerythrityl Hexacaprylate/Hexacaprate | 19.4 |
| Castor oil | | 19.2 |
| Isofol ester 0604 | | 19.1 |
| Miglyol 840 | Propylene Glycol Dicaprylate/Dicaprate | 18.7 |
| Isofol 12 | Butyl Octanol | 17.4 |
| Tegosoft SH | Stearyl Heptanoate | 17.8 |
| Avocado oil | | 14.5 |
| Cetiol B | Dibutyl Adipate | 14.3 |
| Dermol 488 | PEG-2 Diethylene hexanoate | 10.1 |

Nonpolar oils include, for example, those which are selected from branched and unbranched hydrocarbons and hydrocarbon waxes, in particular vaseline (petrolatum), paraffin oil, squalane and squalene, polyolefins and hydrogenated polyisobutenes. Among the polyolefins, polydecenes are the preferred substances.

Particularly advantageous nonpolar lipids for the purposes of the present invention include the substances listed below:

| Trade name | INCI name | Polarity [mN/m] |
|---|---|---|
| Ecolane 130 | Cycloparaffin | 49.1 |
| Nexbase 2006 FG | Polydecene | 46.7 |
| Polysynlane | Hydrogenated Polyisobutene | 44.7 |
| Wacker Silicone oil AK 50 | Polydimethylsiloxane | 46.5 |
| Solvent ICH | Isohexadecane | 43.8 |
| Pionier 2076 | Mineral Oil | 43.7 |
| Pionier 6301 | Mineral Oil | 43.7 |
| Wacker Silicone Oil AK 35 | Polydimethylsiloxane | 42.4 |
| Isoeicosane | Isoeicosane | 41.9 |
| Wacker Silicone oil AK 20 | Polydimethylsiloxane | 40.9 |
| Isofol 1212 carbonate | | 40.3 |
| Softcutol O | Ethoxydiglycol Oleate | 40.5 |
| Lipodermanol OL | Decyl Olivate | 40.3 |
| Cetiol S | Dioctylcyclohexane | 39.0 |
| Pionier 2071 | Mineral Oil | 38.3 |
| Hydrobrite 1000 PO | Paraffinum Liquidum | 37.6 |
| Tegosoft HP | Isocetyl Palmitate | 36.2 |
| Isofol Ester 1693 | | 33.5 |
| Isofol Ester 1260 | | 33.0 |
| Dow Corning Fluid 245 | Cyclopentasiloxane | 32.3 |
| Prisorine 2036 | Octyl Isostearate | 31.6 |
| Cetiol CC | Dicaprylyl Carbonate | 31.7 |
| Dermol 99 | Trimethylhexyl Isononanoate | 31.1 |
| Dermol 89 | 2-Ethylhexyl Isononanoate | 31.0 |
| Cetiol OE | Dicaprylyl Ether | 30.9 |
| Dihexyl carbonate | Dihexyl Carbonate | 30.9 |
| Silkflo 366 NF | Polydecene | 30.1 |
| Estol 1540 EHC | Octyl Cocoate | 30.0 |

However, it may also be advantageous to use mixtures of lipids with higher and lower polarity, e.g., a mixture of nonpolar and mid-polar lipids and the like. Thus, the oil phase may advantageously be selected from branched and unbranched hydrocarbons and hydrocarbon waxes, dialkyl ethers, saturated or unsaturated, branched or unbranched alcohols, and fatty acid triglycerides, e.g., the triglycerol esters of saturated and/or unsaturated, branched and/or unbranched alkanecarboxylic acids with a chain length of from about 8 to 24, in particular about 12-18, carbon atoms. The fatty acid triglycerides may, for example, advantageously be selected from synthetic, semisynthetic and natural oils, e.g. olive oil, sunflower oil, soybean oil, peanut oil, rapeseed oil, almond oil, palm oil, coconut oil, palm kernel oil and the like.

Fatty and/or wax components which may advantageously be used according to the invention may be selected from, e.g., vegetable waxes, animal waxes, mineral waxes and petrochemical waxes. According to the invention, candelilla wax, carnauba wax, japan wax, esparto grass wax, cork wax, guaruma wax, rice germ oil wax, sugarcane wax, berry wax, ouricury wax, montan wax, jojoba wax, shea butter, beeswax, shellac wax, spermaceti, lanolin (wool wax), uropygial grease, ceresine, ozokerite (earth wax), paraffin waxes and microcrystalline waxes, for example, may be favourable.

Further advantageous fatty and/or wax components include chemically modified waxes and synthetic waxes, such as, for example, those available under the trade names Syncrowax HRC (glyceryl tribehenate), and Syncrowax AW 1C ($C_{18-36}$-fatty acid) from CRODA GmbH, and montan ester waxes, sasol waxes, hydrogenated jojoba waxes, synthetic or modified beeswaxes (e.g. dimethicone copolyol beeswax and/or $C_{30-50}$-alkyl beeswax), polyalkylene waxes, polyethylene glycol waxes, but also chemically modified fats, such as, for example, hydrogenated plant oils (for example hydrogenated castor oil and/or hydrogenated coconut fatty glycerides), triglycerides, such as, for example, trihydroxystearin, fatty acids, fatty acid esters and glycol esters, such as, for example, $C_{20-40}$-alkyl stearate, $C_{20-40}$-alkylhydroxystearyl stearate and/or glycol montanate. In addition, also advantageous are certain organosilicon compounds which have similar physical properties to said fatty and/or wax components, such as, for example, stearoxytrimethylsilane.

According to the invention, the fatty and/or wax components may either be present individually or as a mixture of two or more thereof. Any mixtures of such oil and wax components can also be used advantageously for the purposes of the present invention.

The oil phase may advantageously be selected from 2-ethylhexyl isostearate, octyldodecanol, isotridecyl isononanoate, butylene glycol dicaprylate/dicaprate, 2-ethylhexyl cocoate, $C_{12-15}$-alkyl benzoate, caprylic/capric triglyceride, dicaprylyl ether and any combinations thereof.

Mixtures of octyldodecanol, caprylic/capric triglyceride, dicaprylyl ether, dicaprylyl carbonate, coco glycerides, or mixtures of $C_{12-15}$-alkyl benzoate and 2-ethylhexyl isostearate, mixtures of $C_{12-15}$-alkyl benzoate and butylene glycol dicaprylate/dicaprate, and mixtures of $C_{12-15}$-alkyl benzoate, 2-ethylhexyl isostearate and isotridecyl isononanoate may be particularly advantageous.

Of the hydrocarbons, paraffin oil, cycloparaffin, squalane, squalene, hydrogenated polyisobutene and/or polydecene may advantageously be used for the purposes of the present invention.

It may likewise be advantageous to select the oil phase of the preparations according to the invention partially or completely from cyclic and/or linear silicones, which are also referred to as "silicone oils" for the purposes of the present disclosure. Such silicones or silicone oils may be present as monomers, which are generally characterized by structural elements, as follows:

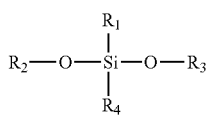

Silicone oils are high molecular weight synthetic polymeric compounds in which silicon atoms are joined via oxygen atoms in a chain-like and/or neticular manner and the remaining valences of the silicon are saturated by hydrocarbon radicals (in most cases methyl groups, less often ethyl, propyl, phenyl groups etc.).

Linear silicones with a plurality of siloxyl units which may advantageously be used according to the invention are generally characterized by structural elements as follows:

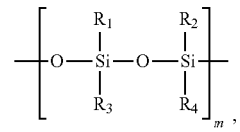

where the silicon atoms may be substituted by identical or different alkyl radicals and/or aryl radicals, which are shown here in general terms by the radicals $R_1$-$R_4$ (that is to say the number of different radicals is not necessarily limited to 4). m can assume values from about 2-200,000.

Systematically, the linear silicone oils are referred to as polyorganosiloxanes. The methyl-substituted polyorganosiloxanes, which represent the most important compounds of this group are usually characterized by the following structural formula

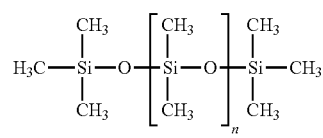

and are also referred to as polydimethylsiloxane and Dimethicone (INCI). Dimethicones have various chain lengths and various molecular weights. Dimethicones of various chain lengths and phenyltrimethicones are particularly advantageous linear silicone oils for the purposes of the present invention.

Particularly advantageous polyorganosiloxanes for the purposes of the present invention are also, for example, dimethylpolysiloxanes [poly(dimethylsiloxane)], which are available, for example, under the trade names ABIL 10 to 10 000 from Th. Goldschmidt. Also advantageous are phenylmethylpolysiloxanes (INCI: Phenyl Dimethicone, Phenyl Trimethicone), cyclic silicones (octamethylcyclotetrasiloxane and decamethylcyclopentasiloxane), which are also referred to according to INCI as cyclomethicones, amino-modified silicones (INCI: Amodimethicones) and silicone waxes, e.g., polysiloxane-polyalkylene copolymers (INCI: Stearyl Dimethicone and Cetyl Dimethicone) and dialkoxydimethylpolysiloxanes (Stearoxy Dimethicone and Behenoxy Stearyl Dimethicone), which are available as various Abil wax grades from Th. Goldschmidt.

Also particularly advantageous for the purposes of the present invention are the silicone oils listed below:

| Trade name | INCI name | Polarity [mN/m] |
|---|---|---|
| Wacker Silicone Oil AK 100 | Polydimethylsiloxane | 26.9 |
| Wacker Silicone Oil AK 50 | Polydimethylsiloxane | 46.5 |
| Wacker Silicone Oil AK 35 | Polydimethylsiloxane | 42.4 |
| Wacker Silicone Oil AK 20 | Polydimethylsiloxane | 40.9 |
| Dow Corning Fluid 245 | Cyclopentasiloxane | 32.3 |
| Dow Corning Fluid 345 | Cyclomethicone | 28.5 |

Cyclic silicones which may advantageously be used according to the invention are generally characterized by structural elements as follows

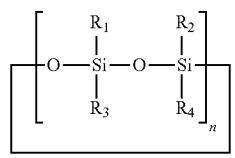

where the silicon atoms may be substituted by identical or different alkyl radicals and/or aryl radicals, which are represented here in general terms by the radicals $R_1$-$R_4$ (that is to say that the number of different radicals is not necessarily limited to 4). n can assume values from 3/2 to 20. Fractional values for n take into consideration the fact that odd numbers of siloxyl groups may be present in the cycle.

Particularly advantageous cyclic silicone oils for the purposes of the present invention include cyclomethicones, in particular cyclomethicone D5 and/or cyclomethicone D6.

Advantageous silicone oils and/or silicone waxes for the purposes of the present invention include cyclic and/or linear silicone oils and silicone waxes.

It is particularly advantageous for the purposes of the present invention to select the ratio of lipids to silicone oils as approximately 1:1 (generally x:y).

Phenyltrimethicone may advantageously be selected as silicone oil. Other silicone oils, for example, dimethicone, phenyldimethicone, cyclomethicone (octamethylcyclotetrasiloxane), for example hexamethylcyclotrisiloxane, polydimethylsiloxane, poly(methylphenylsiloxane), cetyldimethicone, behenoxydimethicone may also advantageously be used for the purposes of the present invention.

Also advantageous are mixtures of cyclomethicone and isotridecyl isononanoate, and mixtures of cyclomethicone and 2-ethylhexyl isostearate.

It may, however, also be advantageous to select silicone oils of similar constitution to the above-named compounds, whose organic side chains are derivatized, for example polyethoxylated and/or polypropoxylated. These include, for example, polysiloxane-polyalkyl-polyether copolymers, such as cetyldimethicone copolyol and cetyldimethicone copolyol (and) polyglyceryl-4 isostearate (and) hexyl laurate.

An optionally used oil component of the cosmetic or dermatological preparation—for example in the form of cleansing emulsions—for the purposes of the present invention may advantageously be selected from esters of saturated and/or unsaturated, branched and/or unbranched alkanecarboxylic acids with a chain length of from about 3 to 30 carbon atoms and saturated and/or unsaturated, branched and/or unbranched alcohols with a chain length of from about 3 to 30 carbon atoms, and from esters of aromatic carboxylic acids and saturated and/or unsaturated, branched and/or unbranched alcohols with a chain length of from about 3 to 30 carbon atoms. Such ester oils can then advantageously be selected from isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g. jojoba oil.

Any mixtures of such oil and wax components may also advantageously be used for the purposes of the present invention. It may in some instances also be advantageous to use waxes, for example cetyl palmitate, as the sole lipid component of the oil phase.

The oil component may advantageously be selected from 2-ethylhexyl isostearate, octyldodecanol, isotridecyl isononanoate, isoeicosane, 2-ethylhexyl cocoate, $C_{12-15}$-alkyl benzoates, caprylic/capric triglycerides, and dicaprylyl ether.

Mixtures of $C_{12-15}$-alkyl benzoates and 2-ethylhexyl isostearate, mixtures of $C_{12-15}$-alkyl benzoates and isotridecyl isononanoate, and mixtures of $C_{12-15}$-alkyl benzoates, 2-ethylhexyl isostearate and isotridecyl isononanoate are particularly advantageous.

Of the hydrocarbons, paraffin oil, squalane and squalene may advantageously be used for the purposes of the present invention.

The oil component may also advantageously have a content of cyclic and/or linear silicone oils, or consist entirely of such oils, although it is preferred to use an additional content of other oil phase components apart from the silicone oil or the silicone oils.

Cyclomethicone (octamethylcyclotetrasiloxane) may advantageously be used as silicone oil according to the invention. However, other silicone oils may also advantageously be used for the purposes of the present invention, for example hexamethylcyclotrisiloxane, polydimethylsiloxane, and poly(methylphenylsiloxane).

Mixtures of cyclomethicone and isotridecyl isononanoate, and of cyclomethicone and 2-ethylhexyl isostearate are particularly advantageous.

The oil component may further advantageously be selected from or include phospholipids. The phospholipids are phosphoric esters of acylated glycerols. Of great importance among the phosphatidylcholines are, for example, the lecithins, which are characterized by the general structure

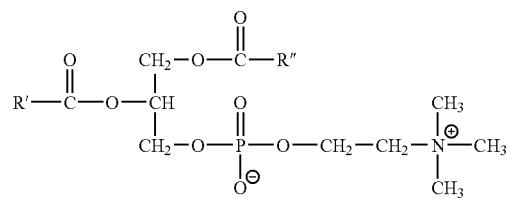

where R' and R" typically are unbranched aliphatic radicals having 15 or 17 carbon atoms and up to 4 cis double bonds.

The lipids referred to as advantageous are naturally only used in the cosmetic preparations according to the invention if they satisfy the polarity according to the claims.

The advantages provided by the W/O or W/S emulsions according to the invention lead to extremely user-friendly cosmetic preparations.

W/O emulsions are a type of classical emulsion. Here, the water droplets are present as internal phase and are surrounded by oil. W/O emulsions do not soak into the skin so quickly. They leave behind a protective fatty film, and consequently have an occlusive action. This film reduces transepidermal water loss (TEWL), thus ensuring intensive skin moisturization and establishing a balanced fat-moisture ratio. Due to their specified features, the W/O emulsions may be used very effectively for dry skin conditions. They are highly suitable for transporting active ingredients into the skin and cannot be removed with water on its own.

W/S emulsions from time to time have a very high silicone oil content and in most cases exhibit a very nice, dry feel on the skin.

Emulsifiers may be added to the preparations according to the invention. According to the invention, the silicone emulsifiers may advantageously be selected from alkyl methicone copolyols and/or alkyl dimethicone copolyols, in particular from compounds which are characterized by the following chemical structure:

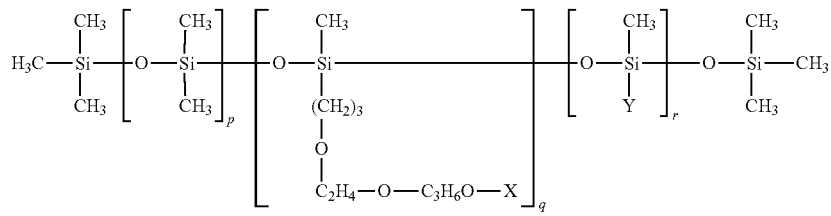

in which X and Y, independently of one another, are selected from H (hydrogen) and branched and unbranched alkyl groups, acyl groups and alkoxy groups having about 1-24 carbon atoms, p is a number from about 0-200, q is a number from about 1-40, and r is a number from about 1-100.

One example of silicone emulsifiers which may particularly advantageously be used for the purposes of the present invention are dimethicone copolyols, which are sold under the trade names ABIL® B 8842, ABIL® B 8843, ABIL® B 8847, ABIL® B 8851, ABIL® B 8852, ABIL® B 8863, ABIL® B 8873 and ABIL® B 88183.

A further example of interface-active substances which may particularly advantageously be used for the purposes of the present invention is cetyl dimethicone copolyol, which is sold under the trade name ABIL® EM 90.

A further example of interface-active substances to be used particularly advantageously for the purposes of the present invention is cyclomethicone dimethicone copolyol, which is sold under the trade name ABIL® EM 97.

In addition, the emulsifier lauryl methicone copolyol, which is available under the trade name Dow Corning® 5200 Formulation Aid, has proven to be very particularly advantageous.

A further advantageous silicone emulsifier is "octyl dimethicone ethoxy glucoside" from Wacker.

According to the invention, the W/O emulsifier or emulsifiers may preferably be selected from the following group: sorbitan stearate, sorbitan oleate, lecithin, glyceryl lanolate, lanolin, microcrystalline wax (Cera microcristallina) in a mixture with paraffin oil (Paraffinum liquidum), ozokerite, hydrogenated castor oil, glyceryl isostearate, polyglyceryl-3 oleate, wool wax acid mixtures, wool wax alcohol mixtures, pentaerythrityl isostearate, polyglyceryl-3 diisostearate, sorbitan oleate in a mixture with hydrogenated castor oil, beeswax (Cera alba) and stearic acid, sodium dihydroxycetylphosphate in a mixture with isopropyl hydroxycetyl ether, methylglucose dioleate, methylglucose dioleate in a mixture with hydroxy stearate and beeswax, mineral oil in a mixture with petrolatum and ozokerite and glyceryl oleate and lanolin alcohol, petrolatum in a mixture with ozokerite and hydrogenated castor oil and glyceryl isostearate and polyglyceryl-3 oleate, PEG-7 hydrogenated castor oil, sorbitan oleate in a mixture with PEG-2 hydrogenated castor oil, ozokerite and hydrogenated castor oil, sorbitan isostearate in a mixture with PEG-2 hydrogenated castor oil, polyglyceryl-4 isostearate, polyglyceryl-4 isostearate, hexyl laurate, acrylate/$C_{10-30}$-alkyl acrylate crosspolymer, sorbitan isostearate, poloxamer 101, polyglyceryl-2 dipolyhydroxystearate, polyglyceryl-3 diisostearate, polyglyceryl-4 dipolyhydroxystearate, PEG-30 dipolyhydroxystearate, diisostearoylpolyglyceryl-3 diisostearate, polyglyceryl-2 dipolyhydroxystearate, polyglyceryl-3 dipolyhydroxystearate, polyglyceryl-4 dipolyhydroxystearate, polyglyceryl-3 dioleate.

The preparations according to the invention may further comprise cosmetic auxiliaries, as are customarily used in such preparations, e.g. preservatives, perfumes, substances for preventing foaming, foam stabilizers, dyes, pigments which have a colouring effect, thickeners, surface-active substances, emulsifiers, softening, moisturizing and/or humectant substances, refatting agents, fats, oils, waxes, alcohols, polyols and toxicologically compatible ethers and esters thereof, branched and/or unbranched hydrocarbons, further antioxidants, stabilizers, pH regulators, consistency-imparting agents, bactericides, deodorants, antimicrobial substances, antistats, UV absorbers, complexing and sequestering agents, pearlizing agents, polymers, electrolytes, organic solvents, silicone derivatives, plant extracts, vitamins and/or other active ingredients or other customary constituents of a cosmetic or dermatological formulation. Solubility promoters, e.g. for incorporating hydrophobic components, such as, for example, perfume preparations, may also be present.

The total amount of the auxiliaries is, for example, from about 0.001% to about 15% by weight, preferably from about 0.01% to about 10% by weight, in each case based on the total weight of the preparation.

The amount of thickeners is, for example, from about 0.05% to about 5.0% by weight, preferably from about 0.1% to about 3.0% by weight, in particular from about 0.15% to about 2.0% by weight, in each case based on the total weight of the preparation.

The water content of the preparations is, for example, from about 60% to about 95% by weight, preferably from about 75% to about 95% by weight, in particular form about 80% to about 90% by weight, in each case based on the total weight of the preparation.

Due to the skin-friendly properties, the preparations according to the invention can be used for cosmetics of all types, in particular as lotion, cream, or else as impregnation solution, spray or aerosol.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those skilled in the art how the several forms of the present invention may be embodied in practice. Unless stated otherwise, all amounts, fractions and percentages given are based on the weight and the total amount or on the total weight of the preparations.

EXAMPLES

W/O Emulsions (Low-Viscosity W/O Emulsions Also for Use as Impregnation Solution, Spray or Aerosol)

| | Example | | | | |
|---|---|---|---|---|---|
| | 1 | 2 | 3 | 4 | 5 |
| Triglycerol diisostearate | 1.0 | 0.5 | 0.25 | 2.0 | 3.0 |
| Diglycerol dipolyhydroxystearate | 1.0 | 1.5 | 1.75 | 3.0 | 2.0 |
| Paraffin oil | 12.5 | 10.0 | 8.0 | 5.0 | 17.5 |
| Vaseline | 8.0 | 6.0 | 5.0 | 12.0 | 2.5 |
| Hydrogenated coconut glycerides | 2.0 | 1.0 | 2.5 | 5.0 | 0.25 |
| Decyl oleate | 0.5 | 0.75 | 1.0 | 2.0 | 0.25 |
| Octyldodecanol | 0.5 | 1.0 | 0.75 | 3.0 | 0.25 |
| Aluminium stearate | 0.4 | 0.3 | 0.6 | 1.0 | 0.05 |
| Dicaprylyl carbonate | 0.1 | 0.05 | 0.15 | 0.5 | 1.0 |
| Hydrogenated castor oil | 0.5 | 0.75 | 1.0 | 2.5 | 5.0 |
| Microcrystalline cellulose | 0.5 | 1.0 | 0.75 | 0.25 | 0.1 |
| Magnesium sulphate | 0.5 | 0.6 | 0.5 | 0.7 | 1.0 |
| Glycerol | 3.0 | 5.0 | 10.0 | 15.0 | 1.5 |
| Citric acid | 0.2 | 0.1 | 0.2 | 0.3 | 1.0 |
| Sodium citrate | 0.4 | 0.2 | 0.4 | 0.6 | 2.0 |
| Perfume | q.s. | q.s. | q.s. | q.s. | q.s. |
| Ethanol | 2.0 | — | 5.0 | — | — |
| Caprylic/capric triglyceride | 2.0 | 2.5 | 3.0 | 5.0 | 0.5 |
| Potassium sorbate | 0.4 | 0.15 | 0.05 | 0.3 | 0.4 |
| Benzyl alcohol | 0.3 | 0.4 | 0.25 | 0.15 | — |
| Dehydracetic acid, Na salt | — | — | 0.05 | — | 0.1 |
| Water | ad 100 | ad 100 | ad 100 | ad 100 | ad 100 |

W/O Emulsions (Low-Viscosity W/O Emulsions Also for Use as Impregnation Solution Spray or Aerosol)

| | Example | | | | |
|---|---|---|---|---|---|
| | 6 | 7 | 8 | 9 | 10 |
| PEG-30 dipolyhydroxystearate | — | 0.5 | 0.25 | — | 3.0 |
| Lanolin alcohol | 1.0 | 1.5 | 1.75 | 3.0 | — |
| Paraffin oil | 12.5 | 10.0 | 8.0 | 5.0 | 17.5 |
| Vaseline | 8.0 | 6.0 | 5.0 | 12.0 | 2.5 |
| Hydrogenated cocoglycerides | 2.0 | 1.0 | 2.5 | 5.0 | 0.25 |
| Hydrogenated polyisobutene | 0.5 | 0.75 | 1.0 | 2.0 | 0.25 |
| Octyldodecanol | 0.5 | 1.0 | 0.75 | 3.0 | 0.25 |
| Aluminium stearate | 0.4 | 0.3 | 0.6 | 1.0 | 0.05 |
| Dicaprylyl carbonate | 0.1 | 0.05 | 0.15 | 0.5 | 1.0 |
| Hydrogenated castor oil | 0.5 | 0.75 | 1.0 | 2.5 | 5.0 |
| Microcrystalline cellulose | 0.5 | 1.0 | 0.75 | 0.25 | 0.1 |
| Magnesium sulphate | 0.5 | 0.6 | 0.5 | 0.7 | 1.0 |
| Glycerol | 3.0 | 5.0 | 10.0 | 15.0 | 1.5 |
| Citric acid | 0.2 | 0.1 | 0.2 | 0.3 | 1.0 |
| Perfume | q.s. | q.s. | q.s. | q.s. | q.s. |
| 1,3-Butylene glycol | 2.0 | — | 5.0 | — | — |
| Caprylic/capric triglyceride | 2.0 | 2.5 | 3.0 | 5.0 | 0.5 |
| Talc, micronized | 1.0 | 0.5 | 5.0 | 0.25 | — |
| Potassium sorbate | 0.3 | 0.4 | 0.25 | 0.15 | — |
| Iminodisuccinate | — | — | 0.05 | — | 0.1 |
| Water | ad 100 | ad 100 | ad 100 | ad 100 | ad 100 |

W/S Emulsions (Low-Viscosity W/S Emulsions Also for Use as Impregnation Solution, Spray or Aerosol)

| | Example | | | | |
|---|---|---|---|---|---|
| | 11 | 12 | 13 | 14 | 15 |
| Cetyl PEG/PPG-10/1 dimethicone | 1.0 | — | — | 3.0 | 5.0 |
| Cyclomethicone + PEG/PPG-18/18 dimethicone (90:10) | 10.0 | 12.5 | 15.0 | — | — |
| Cyclomethicone | 12.5 | 15 | 18.0 | 25.0 | 17.5 |
| Dimethicone | 5.0 | 13.0 | 5.0 | 12.0 | 15.0 |
| Hydrogenated polyisobutene | 0.5 | 0.75 | 1.0 | 2.0 | 0.25 |
| Octyldodecanol | 0.5 | 1.0 | 0.75 | 3.0 | 0.25 |
| Panthenol | 0.5 | 1.0 | 0.75 | 0.25 | 0.1 |
| Sodium chloride | 2.0 | 0.6 | 2.5 | 0.7 | 1.0 |
| Glycerol | 3.0 | 5.0 | 10.0 | 15.0 | 1.5 |
| Lactic acid | 0.2 | — | 1.75 | 0.3 | 1.0 |
| Sodium lactate | 0.4 | — | 3.5 | 0.6 | 2.0 |
| Perfume | q.s. | q.s. | q.s. | q.s. | q.s. |
| Potassium sorbate | 0.4 | 0.1 | 0.05 | 0.3 | 0.5 |
| Microcrystalline cellulose | 1.0 | 0.1 | 0.5 | — | — |
| C5-Cyclomethicone | 1.0 | — | 7.0 | — | — |
| Iodopropynyl butylcarbamate | — | — | 0.05 | — | 0.1 |
| Modified starch | — | 2.5 | — | 0.15 | — |
| Water | ad 100 | ad 100 | ad 100 | ad 100 | ad 100 |

W/S Emulsions (Low-Viscosity W/S Emulsions Also for Use as Impregnation Solution, Spray or Aerosol)

| | Example | | | | |
|---|---|---|---|---|---|
| | 16 | 17 | 18 | 19 | 20 |
| Cetyl PEG/PPG-10/1 dimethicone | 1.0 | — | — | 3.0 | 5.0 |
| Cyclomethicone + PEG/PPG-18/18 dimethicone (90:10) | 10.0 | 12.5 | 25 | — | — |
| Cyclomethicone | 12.5 | 15 | 28.0 | 25.0 | 17.5 |
| Dimethicone | 5.0 | 13.0 | 5.0 | 12.0 | 15.0 |
| Hydrogenated polyisobutene | 0.5 | 0.75 | 1.0 | 2.0 | 0.25 |
| Octyldodecanol | 0.5 | 1.0 | 0.75 | 3.0 | 0.25 |
| Panthenol | 0.5 | 1.0 | 0.75 | 0.25 | 0.1 |
| Sodium chloride | 2.0 | 0.6 | 2.5 | 0.7 | 1.0 |
| Glycerol | 3.0 | 5.0 | 10.0 | 15.0 | 1.5 |
| Citric acid | 0.2 | 0.1 | 0.2 | 0.3 | 1.0 |
| Perfume | q.s. | q.s. | q.s. | q.s. | q.s. |
| Potassium sorbate | 0.4 | 0.1 | 0.05 | 0.3 | 0.4 |
| Microcrystalline cellulose | 1.0 | — | 1.5 | 2.5 | 0.1 |

|  | Example | | | | |
|---|---|---|---|---|---|
|  | 16 | 17 | 18 | 19 | 20 |
| Benzyl alcohol | 0.3 | 0.4 | 1.5 | 0.15 | — |
| Stearyl dimethicone | 0.5 | — | 0.7 | — | — |
| Dehydracetic acid, sodium salt | — | — | 0.05 | — | 0.1 |
| Modified starch | — | 2.5 | — | 0.15 | — |
| Water | ad 100 | ad 100 | ad 100 | ad 100 | ad 100 |

W/O Emulsions (Low-Viscosity W/O Emulsions Also for Use as Impregnation Solution, Spray or Aerosol)

|  | Example | | | | |
|---|---|---|---|---|---|
|  | 21 | 22 | 23 | 24 | 25 |
| PEG-22 Dodecyl glycol copolymer | 5.0 | 1.5 | 0.25 | — | 3.0 |
| PEG-45 Dodecyl glycol polymer | 1.0 | 1.5 | 1.75 | 3.0 | — |
| Paraffin oil | 12.5 | 10.0 | 8.0 | 5.0 | 17.5 |
| Isopropyl stearate | 8.0 | 6.0 | 5.0 | 12.0 | 2.5 |
| Hydrogenated cocoglycerides | 2.0 | 1.0 | 2.5 | 5.0 | 0.25 |
| Evening primrose oil | 0.5 | 0.75 | 1.0 | 2.0 | 0.25 |
| Octyldodecanol | 0.5 | 1.0 | 0.75 | 3.0 | 0.25 |
| Aluminium stearate | 0.4 | 0.3 | 0.6 | 1.0 | 0.05 |
| Dicaprylyl carbonate | 0.1 | 0.05 | 0.15 | 0.5 | 1.0 |
| Hydrogenated castor oil | 0.5 | 0.75 | 1.0 | 2.5 | 5.0 |
| Microcrystalline cellulose | 0.5 | 1.0 | 0.75 | — | — |
| Magnesium sulphate | 0.5 | 0.6 | 0.5 | 0.7 | 1.0 |
| Glycerol | 3.0 | 5.0 | 10.0 | 15.0 | 1.5 |
| Citric acid | 0.2 | 0.1 | 0.2 | 0.3 | 1.0 |
| Perfume | q.s. | q.s. | q.s. | q.s. | q.s. |
| 1,3-Butylene glycol | 2.0 | — | 5.0 | — | — |
| Caprylic/capric triglyceride | 2.0 | 2.5 | 3.0 | 5.0 | 0.5 |
| Benzyl alcohol | — | — | — | 1.0 | 0.75 |
| Potassium sorbate | 0.4 | 0.15 | 0.05 | 0.3 | 0.4 |
| Talc, micronized | 0.3 | 0.4 | 2.5 | — | — |
| Iminodisuccinate | — | — | 0.05 | — | 0.1 |
| Water | ad 100 | ad 100 | ad 100 | ad 100 | ad 100 |

W/O Emulsions (Low-Viscosity W/O Emulsions Also for Use as Impregnation Solution, Spray or Aerosol)

|  | Example | | | | |
|---|---|---|---|---|---|
|  | 26 | 27 | 28 | 29 | 30 |
| Polyglyceryl-2 dipolyhydroxystearate | 3.0 | — | 0.25 | — | 3.0 |
| Polyglyceryl-3 diisostearate | 1.0 | 3.5 | 1.75 | 2.5 | — |
| PEG-40 sorbitan isostearate | — | 2.5 | 0.5 | 3.5 | 3.0 |
| Paraffin oil | 12.5 | 10.0 | 8.0 | 5.0 | 17.5 |
| Isopropyl stearate | 8.0 | 6.0 | 5.0 | 12.0 | 2.5 |
| Hydrogenated cocoglycerides | 2.0 | 1.0 | 2.5 | 5.0 | 0.25 |
| Isopropyl palmitate | 0.5 | 1.0 | 0.75 | 3.0 | 0.25 |
| Dicaprylyl carbonate | 0.1 | 0.05 | 0.15 | 0.5 | 1.0 |
| Potassium sorbate | 0.05 | 0.1 | 0.5 | 0.75 | 0.25 |
| Hydrogenated castor oil | 0.5 | 0.75 | 1.0 | 2.5 | 5.0 |
| Microcrystalline cellulose | 0.5 | 1.0 | 0.75 | — | 0.1 |
| Talc, micronized | 0.5 | 1.0 | — | 0.25 | 0.1 |
| Magnesium sulphate | 0.5 | 0.6 | 0.5 | 0.7 | 1.0 |
| Glycerol | 3.0 | 5.0 | 10.0 | 15.0 | 1.5 |
| Citric acid | 0.2 | 0.09 | 0.2 | 0.3 | 1.0 |
| Sodium citrate | 0.4 | 0.18 | 0.4 | 0.6 | 2.0 |
| Perfume | q.s. | q.s. | q.s. | q.s. | q.s. |
| 1,3-Butylene glycol | 2.0 | — | 5.0 | — | — |
| Caprylic/capric triglyceride | 2.0 | 2.5 | 3.0 | 5.0 | 0.5 |
| Iminodisuccinate | — | — | 0.05 | — | 0.1 |
| Water | ad 100 | ad 100 | ad 100 | ad 100 | ad 100 |

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A cosmetic or dermatological compositions, wherein the composition comprises potassium sorbate, microcrystalline cellulose, and at least one of a perfume, magnesium sulfate, dehydracetic acid, a salt of dehydracetic acid, benzyl alcohol, a citrate buffer, a lactate buffer, and talc, and wherein the composition is suitable for topical application to the skin.

2. The composition of claim 1, wherein the composition comprises from about 0.001% to about 1% by weight of potassium sorbate.

3. The composition of claim 1, wherein the composition comprises from about 0.01% to about 0.6% by weight of potassium sorbate.

4. The composition of claim 2, wherein the composition comprises from about 0.01% to about 5% by weight of microcrystalline cellulose.

5. The composition of claim 3, wherein the composition comprises from about 0.1% to about 1% by weight of microcrystalline cellulose.

6. The composition of claim 1, wherein the composition comprises microcrystalline cellulose having a molecular weight of from about 20,000 to about 80,000 g/mol.

7. The composition of claim 5, wherein the composition comprises microcrystalline cellulose having a molecular weight of from about 30,000 to about 50,000 g/mol.

8. The composition of claim 1, wherein the composition comprises microcrystalline cellulose having a particle size of from about 1 μm to about 100 μm.

9. The composition of claim 6, wherein the composition comprises microcrystalline cellulose having a particle size of from about 10 μm to about 50 μm.

10. The composition of claim 1, wherein the composition is a water-in-oil emulsion.

11. The composition of claim 1, wherein the composition is a water-in-silicone emulsion.

12. The composition of claim 1, wherein the composition further comprises dehydracetic acid and/or a salt thereof.

13. The composition of claim 12, wherein the composition comprises the sodium salt of dehydracetic acid.

14. The composition of claim 12, wherein the composition comprises from about 0.01% to about 2% by weight of dehydracetic acid and/or a salt thereof.

15. The composition of claim 1, wherein the composition comprises benzyl alcohol.

16. The composition of claim 2, wherein the composition comprises from about 0.1% to about 2.0% by weight of benzyl alcohol.

17. The composition of claim 1, wherein the composition comprises at least one of a citrate buffer and a lactate buffer.

18. The composition of claim 2, wherein the composition comprises a citrate buffer comprising citric acid:sodium citrate in a ratio of about 1:2.

19. The composition of claim 2, wherein the composition comprises a lactate buffer comprising lactic acid:sodium lactate in a ratio of about 1:2.

20. The composition of claim 1, wherein the composition comprises one or more electrolytes.

21. The composition of claim 20, wherein the one or more electrolytes comprise at least one of sodium chloride and magnesium sulfate.

22. The composition of claim 2, wherein the composition comprises from about 0.1% to about 5.0% by weight of one or more electrolytes.

23. The composition of claim 1, wherein the composition further comprises at least one lipid having an interfacial tension of at least about 10 mN/m.

24. A cosmetic or dermatological composition, wherein the composition comprises potassium sorbate, talc and one or more of (i) microcrystalline cellulose, (ii) dehydracetic acid and/or a salt thereof, (iii) benzyl alcohol, (iv) a citrate buffer and (v) a lactate buffer.

25. The composition of claim 24, wherein the composition comprises from about 0.01% to about 5% by weight of talc.

26. The composition of claim 24, wherein the composition comprises from about 0.1% to about 1% by weight of talc.

27. The composition of claim 25, wherein the composition comprises from about 0.001% to about 1% by weight of potassium sorbate.

28. The composition of claim 24, wherein the composition comprises from about 0.01% to about 0.6% by weight of potassium sorbate.

29. The composition of claim 24, wherein the composition comprises from about 0.01% to about 5% by weight of microcrystalline cellulose.

30. The composition of claim 25, wherein the composition comprises from about 0.1% to about 1% by weight of microcrystalline cellulose.

31. The composition of claim 24, wherein the composition is a water-in-silicone emulsion.

32. The composition of claim 24, wherein the composition comprises dehydracetic acid and/or a salt thereof.

33. The composition of claim 24, wherein the composition comprises benzyl alcohol.

34. The composition of claim 24, wherein the composition comprises a citrate buffer and/or a lactate buffer.

35. The composition of claim 34, wherein the composition comprises a citrate buffer comprising citric acid:sodium citrate in a ratio of about 1:2 and/or a lactate buffer comprising lactic acid:sodium lactate in a ratio of about 1:2.

36. The composition of claim 24, wherein the composition further comprises at least one lipid having an interfacial tension of at least about 10 mN/m.

37. A cosmetic or dermatological compositions, wherein the composition comprises potassium sorbate and at least one substance having an interfacial tension of at least about 10 mN/m which is selected from dialkyl ethers, $C_{12-15}$ alkyl benzoates, and Guerbet alcohols.

38. The composition of claim 37, wherein the composition comprises at least one lipid having an interfacial tension of at least about 20 mN/m.

39. The composition of claim 37, wherein the composition comprises at least one lipid having an interfacial tension of at least about 30 mN/m.

40. The composition of claim 37, wherein the composition is a water-in-oil emulsion.

41. The composition of claim 37, wherein the composition is a water-in-silicone emulsion.

42. The composition of claim 37, wherein the composition further comprises dehydracetic acid and/or a salt thereof.

43. The composition of claim 37, wherein the composition further comprises benzyl alcohol.

44. A composition of claim 37, wherein the at least one substance having an interfacial tension of at least about 10 mN/m comprises at least one Guerbet alcohol.

* * * * *